US00PP33244P2

(12) United States Plant Patent
Oates

(10) Patent No.: US PP33,244 P2
(45) Date of Patent: Jul. 6, 2021

(54) ***ECHEVERIA* PLANT NAMED 'MOBEC 69'**

(50) Latin Name: ***Echeveria* hyrbid**
Varietal Denomination: MOBEc 69

(71) Applicant: Morgan Oates & Brown Pty Ltd, Macquarie Fields (AU)

(72) Inventor: John Oates, Millingandi (AU)

(73) Assignee: Morgan Oates & Brown Pty Ltd, Macquarie Fields (AU)

( * ) Notice: Subject to any disclaimer, the term of this patent is extended or adjusted under 35 U.S.C. 154(b) by 0 days.

(21) Appl. No.: 17/021,556

(22) Filed: Sep. 15, 2020

(51) Int. Cl.
*A01H 5/12* (2018.01)
*A01H 6/32* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen M Redden
(74) *Attorney, Agent, or Firm* — Samuel R. McCoy, Jr.

(57) ABSTRACT

A new and distinct *Echeveria* plant named 'MOBEc 69' which is characterized by succulent foliage tightly held in a basal rosette, light blue-green foliage which is lightly margined red, and significantly delayed development of clonal offsets. The new variety has shown to be uniform and stable in the resulting generations from asexual propagation.

4 Drawing Sheets

Latin name of the genus and species: The Latin name of the genus and species of the novel variety disclosed herein is *Echeveria* hybrid.

Variety denomination: The inventive variety of *Echeveria* disclosed herein has been given the variety denomination 'MOBEc 69'.

BACKGROUND OF THE INVENTION

Parentage: 'MOBEc 69' is a seedling selection resulting from the controlled cross-pollination of a proprietary interspecific hybrid seed parent, *Echeveria* hybrid '2027' (not patented), and a proprietary interspecific hybrid pollen parent, *Echeveria* hybrid '2167' (not patented). The crossing was made by the inventor in October of 2012 at a commercial greenhouse in Yowrie, New South Wales, Australia. Seeds were harvested from the seed parent and subsequently grown to a mature size at a secure greenhouse in Picton, New South Wales, Australia. One seedling resulting from said cross was observed to exhibit unique growth and foliage characteristics and was isolated for further evaluation in order to confirm the distinctness and stability of the characteristics first observed. Upon confirmation of distinctness and stability, 'MOBEc 69' was selected for commercialization in the March of 2014.

Asexual Reproduction: Asexual reproduction of the new cultivar 'MOBEc 69', by way of meristematic tissue culture, was first initiated in May of 2016 at a commercial greenhouse in Sleidinge, Belgium. Through 10 subsequent generations, the unique features of this cultivar have proven to be stable and true to type.

SUMMARY OF THE INVENTION

The cultivar 'MOBEc 69' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'MOBEc 69'. These characteristics in combination distinguish 'MOBEc 69' as a new and distinct *Echeveria* cultivar:

1. *Echeveria* 'MOBEc 69' exhibits a compact rosette of tightly-held, succulent foliage; and
2. *Echeveria* 'MOBEc 69' exhibits greyed-green juvenile foliage and yellow-green mature foliage; and
3. *Echeveria* 'MOBEc 69' exhibits foliage which is moderately covered with light greyed-green epicuticular wax, lending the foliage a blue-green general coloration; and
4. *Echeveria* 'MOBEc 69' exhibits foliar margins that are lightly suffused red; and
5. *Echeveria* 'MOBEc 69' exhibits significantly delayed development of clonal offsets, commonly known as pups.

BOTANICAL DESCRIPTION OF THE PLANT

Figure 1:
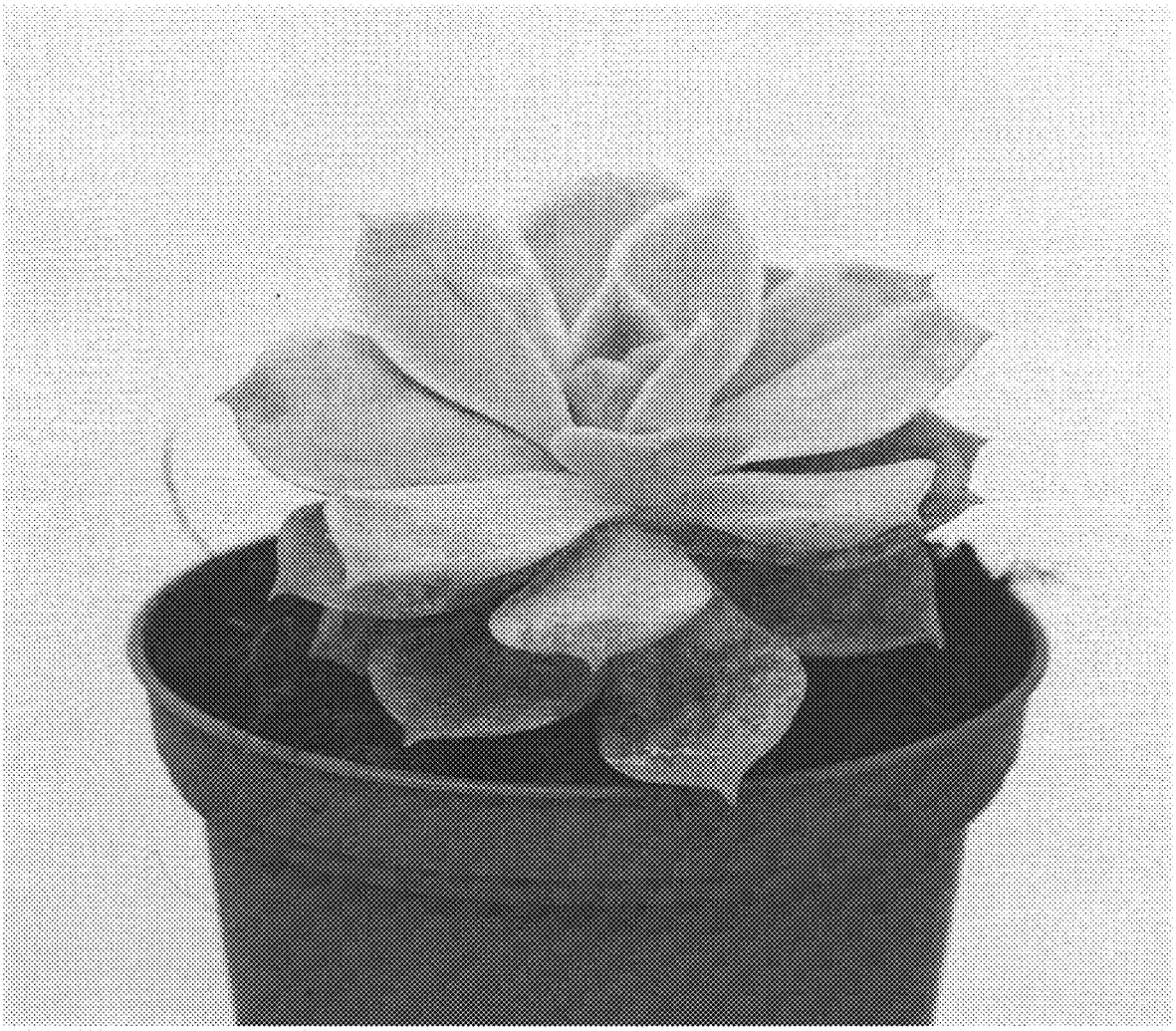
FIG. 1 illustrates, as nearly true as it is reasonably possible to make the same in color photographs of this type, an exemplary plant of 'MOBEc 69' grown in a commercial greenhouse in Sleidinge, Belgium. This plant is approximately 8 months old, shown planted in a 12 cm container.
Figure 2:
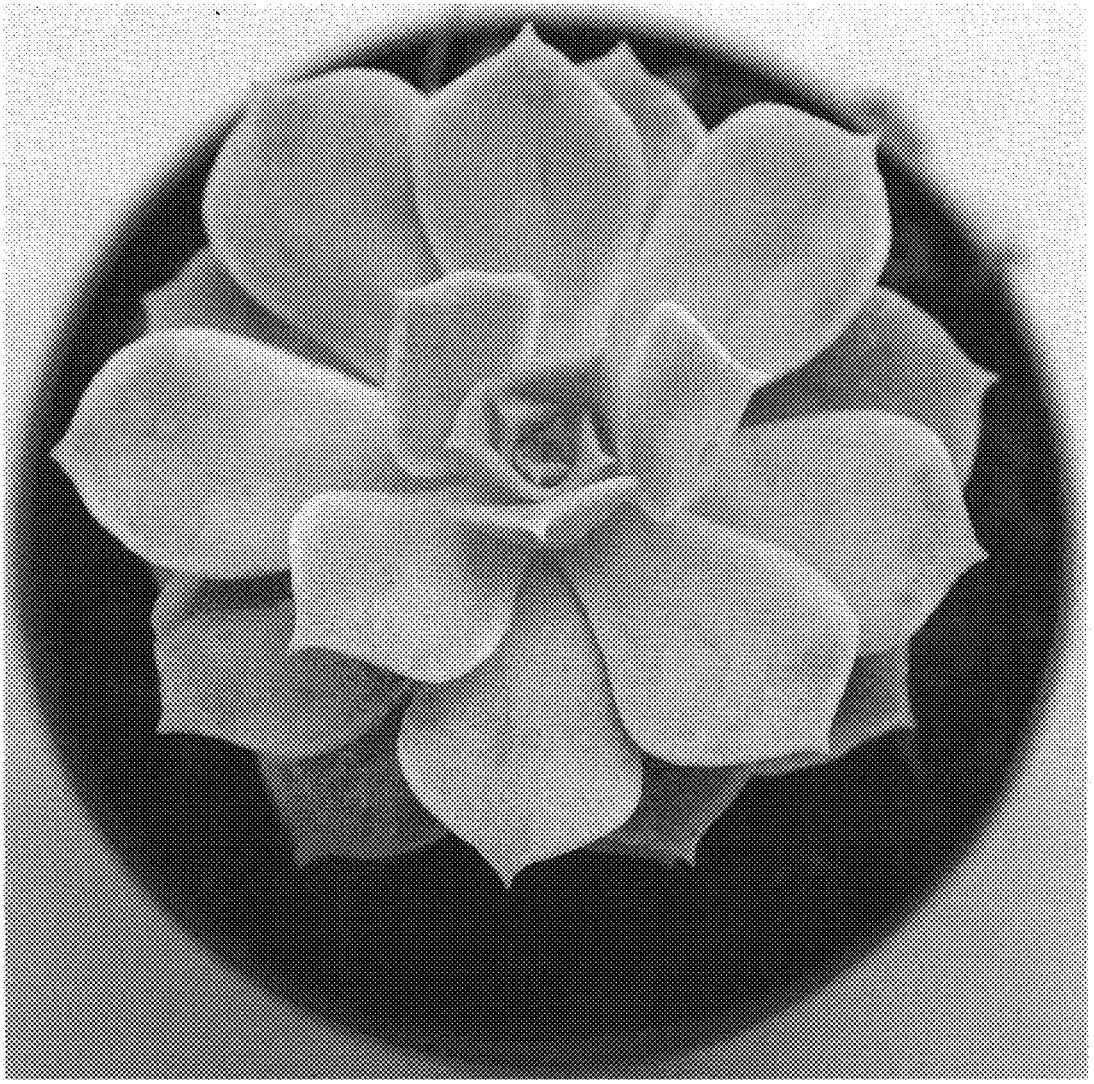
FIG. 2 illustrates, as nearly true as it is reasonably possible to make the same in color photographs of this type, the typical foliage arrangement of 'MOBEc 69'.
Figure 3:
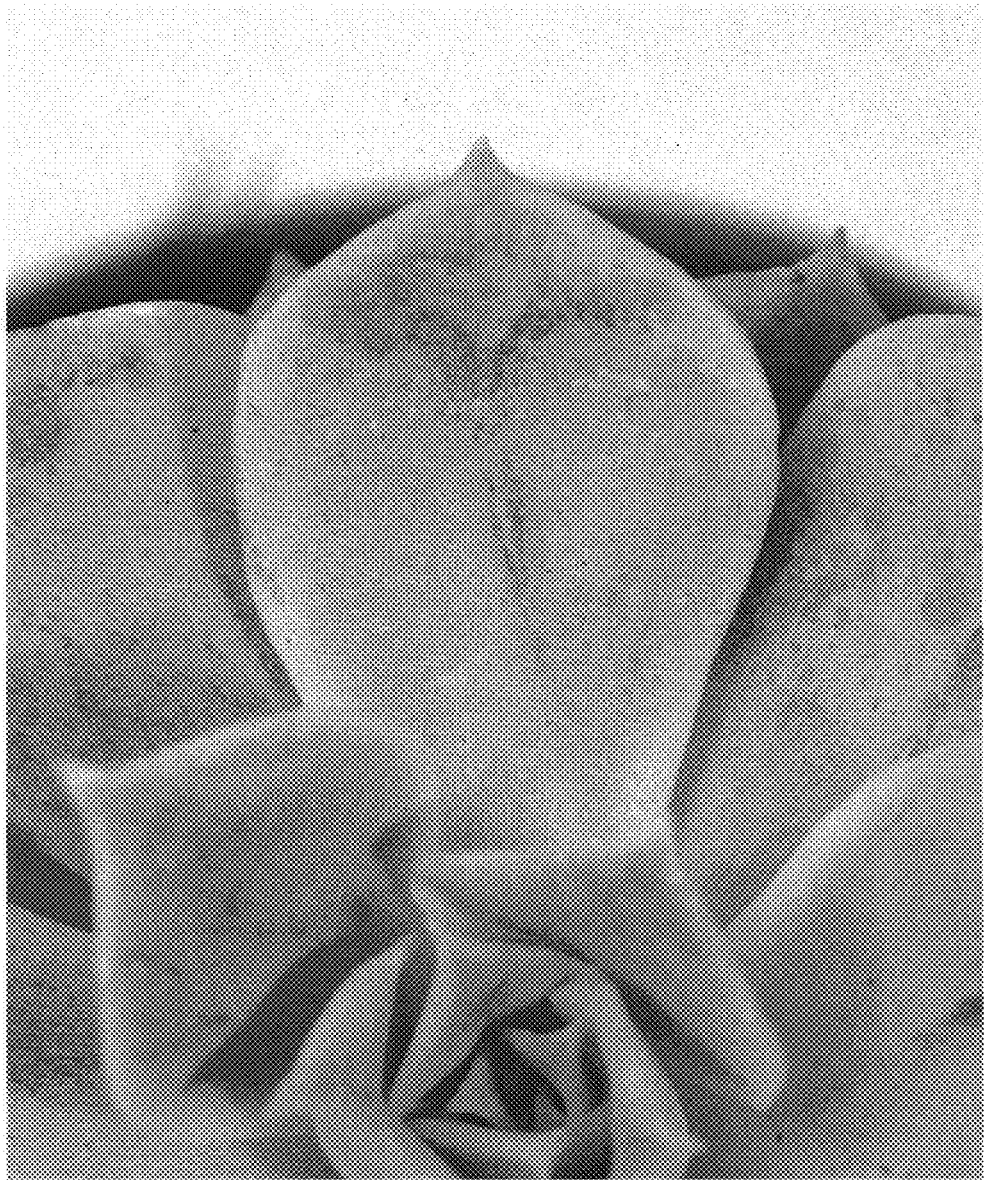
FIG. 3 illustrates, as nearly true as it is reasonably possible to make the same in color photographs of this type, the adaxial surface of the juvenile and mature foliage of 'MOBEc 69'.
Figure 4:
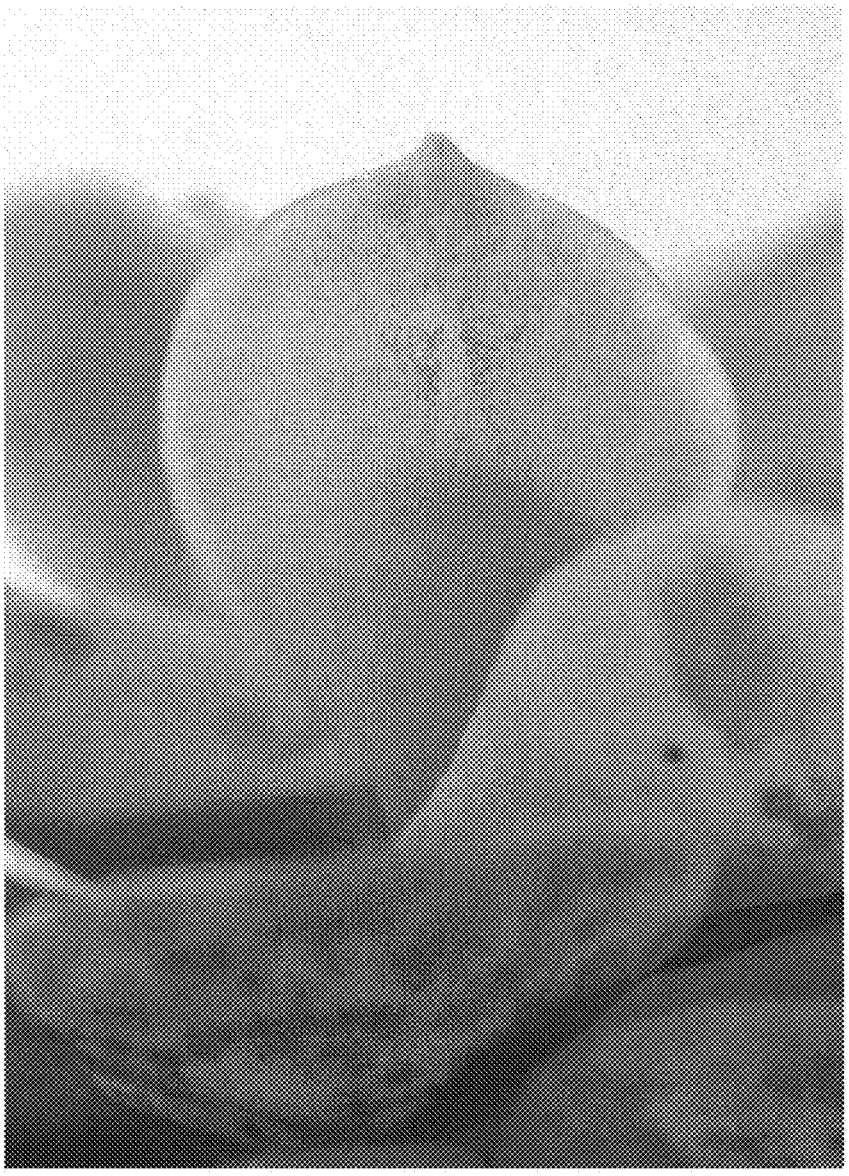
FIG. 4 illustrates, as nearly true as it is reasonably possible to make the same in color photographs of this type, the abaxial surface of the mature foliage of 'MOBEc 69'.

The following observations and measurements made in August of 2018 describe averages from a sample set of six specimens of 6 months old 'MOBEc 69' plants grown in 6.5 cm nursery containers at commercial greenhouse in Sleidinge, Belgium. Plants were produced using conventional greenhouse production protocols for *Echeveria* which consisted of approximately 10,000 lux of light exposure, minimal overhead irrigation and liquid fertilizer applications. No chemical control measures for disease or insect pests were utilized.

Those skilled in the art will appreciate that certain characteristics will vary with older or, conversely, with younger plants. 'MOBEc 69' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'MOBEc 69' and comparisons with the parents and closest known comparator are provided below.

Plant description:

*Growth habit*.—Succulent perennial with foliage growing in a tightly held basal rosette; eventually bearing clonal offsets, commonly known as "pups".

*Plant profile*.—Flattened globular.

*Height from soil level to top of foliar plane*.—4.2 cm.

*Plant spread*.—Average of 5.6 cm.

*Growth rate*.—Slow.

*Plant vigor*.—Moderately vigorous.

*Propagation*.—Type — Meristematic tissue culture. Time to initiate rooting — Approximately 2 weeks at an approximate temperature of 22 degrees Celsius. Crop time — Approximately 9 to 12 months to produce a marketable plant in a 12 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves in a basal rosettes, eventually forming a short, unbranched stem with age; no lateral branching.

*Dimensions*.—3.2 cm long and 0.4 cm in diameter.

*Internode length*.—0.2 cm.

*Cross section*.—Rounded.

*Aspect*.—At an angle of approximately 30 degrees from vertical.

*Strength*.—Moderately strong.

*Texture and luster*.—Glabrous and matte.

*Color when developing*.—Greyed-green, nearest to a mixture of RHS 193A and 193B, and covered with epicuticular wax which is colored greyed-green, RHS 192D.

*Mature color*.—Greyed-green, nearest to a mixture of RHS 193A and 193B, and covered with epicuticular wax which is colored greyed-green, RHS 192D.

*Color at internodes*.—Greyed-green, nearest to a mixture of RHS 193A and 193B, and covered with epicuticular wax which is colored greyed-green, RHS 192D.

Foliage:

*Arrangement*.—Rosette.

*Division*.—Simple.

*Attachment*.—Sessile.

*Quantity*.—Approximately 30 leaves per rosette.

*Shape*.—Broad obovate.

*Dimensions*.—2.5 cm long, 1.4 cm wide, and 0.5 cm thick, on average.

*Aspect*.—Slightly concave.

*Attitude*.—Younger foliage near the center of the rosette is upright; foliage becoming progressively more relaxed towards the outer whorl of the rosette, at an angle of approximately 5 degrees to horizontal.

*Apex*.—Short apiculate.

*Base*.—Cuneate.

*Margin*.—Entire; not undulated or lobed.

*Pubescence, texture and luster of the adaxial surface*.—Glabrous, smooth, and matte; moderately glaucous.

*Pubescence, texture and luster of the abaxial surface*.—Glabrous, smooth, and matte; slightly glaucous.

*Color*.—Juvenile foliage, adaxial surface — Greyed-green, nearest to RHS 191A, and narrowly margined a light yellow-green, nearest to RHS 147D; margins lightly suffused with red, RHS 55C. The epicuticular glaucous wax covering the leaf surface is greyed-green, nearest to RHS 188A. Juvenile foliage, abaxial surface — Greyed-green, nearest to RHS 191A, and margined a light yellow-green, nearest to RHS 147D; margins lightly suffused with red, RHS 55C. The leaf tip is colored greyed-red, RHS 182A. The epicuticular glaucous wax covering the leaf surface is greyed-green, nearest to RHS 188A. Mature foliage, adaxial surface — Yellow-green, nearest to RHS 1468, and margined a lighter shade of yellow-green, nearest to a mixture of RHS 152C and 152D; margins lightly suffused with red, RHS 55C. The epicuticular glaucous wax covering the leaf surface is greyed-green, nearest to RHS 188A. Mature foliage, abaxial surface — Yellow-green, nearest to RHS 1488, and narrowly margined a lighter shade of yellow-green, nearest to RHS 147D; margins lightly suffused with red, RHS 55C. The leaf tip is colored greyed-red, RHS 182A. The epicuticular glaucous wax covering the leaf surface is greyed-green, nearest to RHS 188A.

*Venation*.—Pattern — No venation is visible. Color, adaxial surface — No venation is visible. Color, abaxial surface — No venation is visible.

*Petiole*.—No petiole; leaves are sessile.

Inflorescence: No flowering has been observed to date.

COMPARISONS WITH THE PARENT PLANT AND CLOSEST KNOWN COMPARATOR

Plants of the new cultivar 'MOBEc 69' differ from the seed parent, '2027' (not patented), in the following characteristics described in Table 1 below.

TABLE 1

| Characteristic | 'MOBEc 69' | '2027' |
|---|---|---|
| Plant size. | Larger than '2027'. | Smaller than 'MOBEc 69'. |
| Foliage arrangement. | More tightly held than the foliage of '2027'. | More loosely held than 'MOBEc 69'. |
| General coloration of the mature foliage. | Greyed-green epicuticular wax lends the foliage a blue-green general coloration. | Greyed-green and suffused with pink. |
| Time to offsetting. | Significantly later than '2027'. | Much earlier than 'MOBEc 69'. |

Plants of the new cultivar 'MOBEc 69' differ from the pollen parent, '2176' (not patented), in the following characteristics described in Table 2 below.

TABLE 2

| Characteristic | 'MOBEc 69' | '2176' |
|---|---|---|
| Foliage aspect. | Strongly concaved and strongly curled upwards. | Moderately concaved and slightly curled upward to flat. |
| General coloration of the mature foliage. | Greyed-green epicuticular wax lends the foliage a blue-green general coloration. | Light greyed-red, generally appearing as pink. |

COMPARISONS WITH THE CLOSEST KNOWN COMMERCIAL COMPARATOR

Plants of the new cultivar 'MOBEc 69' differ from the most similar commercial variety known to the inventor, *Echeveria* 'Lola' (not patented), in the following characteristics described in Table 2 below.

TABLE 3

| Characteristic | 'MOBEc 69' | 'Lola' |
|---|---|---|
| Plant size. | Larger than 'Lola'. | Smaller than 'MOBEc 69'. |
| Time to offsetting. | Significantly later than 'Lola'. | Much earlier than 'MOBEc 69'. |
| Foliage arrangement. | More tightly held than the foliage of 'Lola'. | More loosely held than 'MOBEc 69'. |
| General coloration of the mature foliage. | Greyed-green epicuticular wax lends the foliage a blue-green general coloration. | Light greyed-red, generally appearing as pink. |

That which is claimed is:

1. A new and distinct variety of *Echeveria* plant named 'MOBEc 69', substantially as described and illustrated herein.

* * * * *